(12) United States Patent
Kudo et al.

(10) Patent No.: US 7,959,622 B2
(45) Date of Patent: Jun. 14, 2011

(54) SANITARY NAPKIN

(75) Inventors: Jun Kudo, Mitoyo-gun (JP); Takuya Miyama, Mitoyo-gun (JP)

(73) Assignee: Uni-Charm Corporation, Shikikuchuo-shi (JP)

( * ) Notice: Subject to any disclaimer, the term of this patent is extended or adjusted under 35 U.S.C. 154(b) by 367 days.

(21) Appl. No.: 11/344,915

(22) Filed: Jan. 31, 2006

(65) Prior Publication Data

US 2006/0189954 A1   Aug. 24, 2006

(30) Foreign Application Priority Data

Feb. 23, 2005  (JP) ................. 2005-047320

(51) Int. Cl.
*A61F 13/15* (2006.01)

(52) U.S. Cl. ............ 604/385.201; 604/385.19; 604/380; 604/385.01

(58) Field of Classification Search ............. 604/385.01, 604/385.201, 385.19, 380
See application file for complete search history.

(56) References Cited

U.S. PATENT DOCUMENTS

| | | | | |
|---|---|---|---|---|
| 4,326,528 A * | 4/1982 | Ryan et al. | ............... | 604/385.26 |
| 4,738,675 A * | 4/1988 | Buckley et al. | ............... | 604/380 |
| 4,886,513 A * | 12/1989 | Mason et al. | ............ | 604/385.31 |
| 5,053,029 A * | 10/1991 | Yang | ........................ | 604/385.23 |
| 5,197,959 A * | 3/1993 | Buell | ........................ | 604/385.23 |
| 5,300,055 A * | 4/1994 | Buell | ........................ | 604/385.23 |
| 5,382,246 A * | 1/1995 | Kawano | .................... | 604/385.24 |
| 5,486,166 A * | 1/1996 | Bishop et al. | ................. | 604/366 |
| 5,591,149 A * | 1/1997 | Cree et al. | ...................... | 604/378 |
| 5,591,150 A * | 1/1997 | Olsen et al. | ............... | 604/385.23 |
| 5,601,544 A * | 2/1997 | Glaug et al. | ............... | 604/385.28 |
| 5,658,269 A * | 8/1997 | Osborn et al. | ............ | 604/385.16 |
| 5,662,633 A * | 9/1997 | Doak et al. | ...................... | 604/378 |
| 5,662,634 A * | 9/1997 | Yamamoto et al. | ............ | 604/378 |
| 6,160,197 A * | 12/2000 | Lassen et al. | ................... | 604/358 |
| 6,198,019 B1 * | 3/2001 | Hansson et al. | ............... | 604/378 |
| 6,328,724 B1 * | 12/2001 | Ronnberg et al. | ......... | 604/385.24 |
| 6,503,233 B1 * | 1/2003 | Chen et al. | ............... | 604/385.01 |
| 6,520,945 B1 * | 2/2003 | Hansson | ................... | 604/385.24 |
| 6,673,982 B1 * | 1/2004 | Chen et al. | ..................... | 604/378 |
| 6,802,832 B2 * | 10/2004 | Hansson et al. | .......... | 604/385.01 |
| 7,145,054 B2 * | 12/2006 | Zander et al. | .................. | 604/380 |

(Continued)

FOREIGN PATENT DOCUMENTS

EP    293208 A1 * 11/1988

(Continued)

OTHER PUBLICATIONS

Definitions of "slot", "slit", "compressing" and "crimping", Merriam Webster OnLine.*

(Continued)

*Primary Examiner* — Jacqueline F Stephens
(74) *Attorney, Agent, or Firm* — Morrison & Foerster LLP

(57) ABSTRACT

A sanitary napkin includes a liquid-permeable topsheet, a backsheet, and a liquid-absorbent layer disposed between the topsheet and the backsheet. The liquid-absorbent layer has a vagina-facing region on a longitudinal centerline of the sanitary napkin and side regions on both sides of the vagina-facing region. The liquid-absorbent layer has a greater thickness and a greater bending stiffness in the vagina-facing region than in the side regions to provide hinge lines along boundaries between the vagina-facing region and the side regions.

15 Claims, 13 Drawing Sheets

U.S. PATENT DOCUMENTS

| | | | |
|---|---|---|---|
| 2002/0123732 A1* | 9/2002 | Koyama et al. | 604/385.24 |
| 2003/0225385 A1* | 12/2003 | Glaug et al. | 604/385.01 |
| 2004/0204698 A1* | 10/2004 | Zenker et al. | 604/367 |
| 2006/0047257 A1* | 3/2006 | Raidel et al. | 604/383 |
| 2007/0074381 A1* | 4/2007 | Raycheck et al. | 24/452 |
| 2007/0244455 A1* | 10/2007 | Hansson et al. | 604/385.201 |

FOREIGN PATENT DOCUMENTS

| | | |
|---|---|---|
| EP | 391814 A2 * | 10/1990 |
| EP | 1078617 A2 * | 2/2001 |
| JP | 05-095973 A | 4/1993 |
| JP | 06-296644 A | 10/1994 |
| JP | 2002-238948 A | 8/2002 |
| JP | 2003-533236 | 11/2003 |
| JP | 2004-073759 A | 3/2004 |
| JP | 2004-089392 A | 3/2004 |
| JP | 2004-229766 | 8/2004 |
| WO | WO-01/24754 | 4/2001 |

OTHER PUBLICATIONS

Japanese Office Action mailed on Sep. 28, 2010 directed to Japanese Application No. 2005-047320; (4 pages).

* cited by examiner

SANITARY NAPKIN

CROSS REFERENCE TO RELATED APPLICATION

This application claims benefit under 35 U.S.C. 119 from Japanese Patent Application No. 2005-047320, filed on Feb. 23, 2005, which is hereby incorporated by reference in its entirety.

BACKGROUND OF THE INVENTION

1. Field of the Invention

The present invention relates to a sanitary napkin to be worn in the woman's crotch and more particularly to a sanitary napkin whose vagina-facing region can easily fit against the vaginal opening when the sanitary napkin is put on along with an undergarment.

2. Description of the Related Art

Typically, sanitary napkins include a liquid-permeable topsheet lying on a body surface side, a liquid-impermeable backsheet lying on a garment surface side, and a liquid-absorbent layer disposed between the topsheet and the backsheet.

Such sanitary napkins are generally put on along with an undergarment. More specifically, the undergarment is pulled up with the sanitary napkin fixed on an inner side of a crotch part of the undergarment through a pressure-sensitive adhesive layer provided on the backsheet.

When the sanitary napkin is worn in the crotch, it is required that a vagina-facing region, which extends over a given area and lies on a longitudinal centerline of the sanitary napkin, faces the vaginal opening with a minimum of twist. If the vagina-facing region of the sanitary napkin faces the vaginal opening without twist, menstrual blood discharged from the vaginal opening can readily be absorbed by the liquid-absorbent layer, effectively preventing leakage of menstrual blood out of the sanitary napkin. If the vagina-facing region faces the vaginal opening in a twisted state, on the other hand, contact between the body surface of the sanitary napkin and the vaginal opening tends to decrease, resulting in leakage of menstrual blood out of the sanitary napkin.

Japanese Unexamined Patent Application Publication Nos. 2004-89392 and 2004-73759 disclose sanitary napkins whose vagina-facing region can easily fit against the vaginal opening.

In the sanitary napkin disclosed in the Patent Publication No. 2004-89392, secondary absorbent cores are laid on a primary absorbent core to provide a bulky central region on a longitudinal centerline of the sanitary napkin. This bulky region is intended to face the vaginal opening.

In the sanitary napkin disclosed in the Patent Publication No. 2004-73759, a compression line where a topsheet and an absorbent core are compressed and recessed is provided to define a central region on a body surface of the sanitary napkin. In this central region, a low-density liquid guide layer is disposed between the absorbent core and the topsheet. The central region defined by the compression line provides a protuberance which is intended to face the vaginal opening.

Japanese Unexamined Patent Application Publication No. 2002-238948 discloses a sanitary napkin with upper and lower absorbent cores. Both the upper and lower absorbent cores lie in a central region, while only the upper absorbent core lies in side regions on both sides of the central region. When this sanitary napkin is worn in the crotch, the side regions can readily be deformed downwardly to have the central region protrude toward the vaginal opening.

In general, the liquid-absorbent layer has a width of about 80 mm at a location intended to face the vaginal opening; but across the vaginal opening, the human's crotch has a width of about 30 mm, which varies between individuals, though. Accordingly, when the sanitary napkin is adhered on the undergarment and pulled up along with the undergarment, the side portions of the liquid-absorbent layer tend to be deformed or twisted on the way to the crotch, which leads to tilt or deformation of the vagina-facing region. When the sanitary napkin is applied to the crotch, therefore, it is difficult for the vagina-facing region to closely fit against the vaginal opening.

In the sanitary napkin disclosed in the Patent Publication No. 2004-89392, although the central region is made bulky by laying one absorbent core on the other, since the upper absorbent core is not secured on the lower absorbent core, the liquid-absorbent layer does not have a large stiffness difference between the central region and side regions on both sides of the central region. Accordingly, when the side regions are compressed between the thighs on the way to the crotch, the sanitary napkin tends to be deformed as a whole.

In the sanitary napkin disclosed in the Patent Publication No. 2004-73759, since the compression line is provided to surround the central region, there is an advantage that the side portions of the liquid-absorbent layer easily fold on the compression line. However, since the compression line is formed by heating and pressing the absorbent core and the topsheet to increase density, it is not sufficiently flexible to function as a hinge line. In addition, since there is not much stiffness difference between the central region surrounded by the compression line and the side regions outside the compression line, when the thighs exert pressure on both sides of the sanitary napkin, the absorbent core tends to be compressed not only in the side regions but also in the central region, which results in folding of the central region.

In the sanitary napkin disclosed in the Patent Publication No. 2002-238948, since both the upper and lower absorbent bodies are made of a fiber aggregate such as fluff pulp, there is not much stiffness difference between the central region and the side regions. When worn in the crotch, therefore, the sanitary napkin tends to be curved as a whole, which makes it difficult for the central region to face the vaginal opening in a flattened state.

SUMMARY OF THE INVENTION

The present invention has been developed to solve the problems in the prior art set forth above and has an object to provide a sanitary napkin which is adapted to prevent a vagina-facing region from tilting or folding when the sanitary napkin is put on the crotch, ensuring that the vagina-facing region faces the vaginal opening in an almost flat, undeformed state.

According to a first aspect of the present invention, there is provided a sanitary napkin comprising a liquid-permeable topsheet, a backsheet, and a liquid-absorbent layer disposed between the topsheet and the backsheet, wherein the liquid-absorbent layer has a vagina-facing region on a longitudinal centerline of the sanitary napkin and side regions on both sides of the vagina-facing region, and the liquid-absorbent layer has a greater thickness and a greater bending stiffness in the vagina-facing region than in the side regions to provide hinge lines along boundaries between the vagina-facing region and the side regions.

In the sanitary napkin according to the first aspect of the present invention, the relatively thick vagina-facing region of the liquid-absorbent layer ensures contact of the sanitary napkin with the vaginal opening.

Furthermore, when the sanitary napkin is put on the crotch, the side regions can easily fold on the hinge lines. Therefore, the relatively stiff vagina-facing region is effectively prevented from curving or twisting. Since the vagina-facing region can face the vaginal opening in an almost flat, undeformed state, the vagina-facing region can closely fit against the vaginal opening. On the other hand, since the side regions thus folded can easily fit against the crotch or the thighs, menstrual blood flowing laterally of the sanitary napkin can be effectively collected by the side regions of the liquid-absorbent layer.

In a preferred embodiment of the first aspect of the present invention, the liquid-absorbent layer is constructed of a lower absorbent core and an upper absorbent core secured on a body surface of the lower absorbent core, the lower absorbent core lies in both the vagina-facing region and the side regions, and the upper absorbent core has a smaller area than the lower absorbent core and lies only within the vagina-facing region. The upper absorbent core may be secured on the lower absorbent core through an adhesive or by providing laterally opposing side portions of the upper absorbent core with compression portions where the upper and lower absorbent cores are compressed together. The integration of the lower and upper absorbent cores increases the bending stiffness of the vagina-facing region, thereby increasing the stiffness difference between the vagina-facing region and the side regions. Both the lower and upper absorbent cores are preferably an absorbent sheet whose hydrophilic fibers are bonded together through a binder. Since such an absorbent sheet is considerably stiff, the stiffness difference between the vagina-facing region and the side regions can be increased to facilitate folding of the side regions on the hinge lines.

In another preferred embodiment of the first aspect of the present invention, the liquid-absorbent layer is constructed of a lower absorbent core and an upper absorbent core disposed on a body surface of the lower absorbent core, the lower absorbent core lies in both the vagina-facing region and the side regions, and the upper absorbent core has a smaller area than the lower absorbent core and lies only within the vagina-facing region, wherein the vagina-facing region has a plurality of high-density portions where the lower absorbent core is locally compressed. Preferably, the lower absorbent core has a greater basis weight and a greater density in the vagina-facing region than in the side regions. Providing the vagina-facing region with the high-density portions is particularly effective in a case where the absorbent cores are pulp layers remaining unbonded to each other. Also preferably, the liquid-absorbent layer has a front region in front of the vagina-facing region and the side regions and a rear region behind the vagina-facing region and the side regions, and the lower absorbent core has a greater bending stiffness in the front and rear regions than in the side regions. In this construction, since the side regions are the most deformable, the sanitary napkin can be applied to the crotch without causing deformation of the vagina-facing region, the front region, and the rear region.

In the first aspect of the present invention, a difference in Gurley stiffness between the vagina-facing region and the side regions is preferably at least 1.96 mN (200 mgf), more preferably at least 2.94 mN (300 mgf).

According to a second aspect of the present invention, there is provided a sanitary napkin comprising
a liquid-permeable topsheet,
a backsheet, and
a liquid-absorbent layer disposed between the topsheet and the backsheet,
wherein the liquid-absorbent layer has a vagina-facing region on a longitudinal centerline of the sanitary napkin and side regions on both sides of the vagina-facing region,
the liquid-absorbent layer has an absorbent core with hinge lines along boundaries between the vagina-facing region and the side regions, and
the hinge lines have cuts penetrating through a thickness of the absorbent core or partway into the absorbent core or low-density portions where a density of the absorbent core is locally decreased.

In the sanitary napkin according to the second aspect of the present invention, the cuts or the low-density portions ensure that the side regions fold on the hinge lines.

The hinge lines may lie on both sides of the longitudinal centerline and extend in parallel to the longitudinal centerline. Alternatively, the hinge lines may lie on both sides of the longitudinal centerline and extend arcuately to have an intermediate portion closer to the longitudinal centerline.

In the second aspect of the present invention, preferably, the absorbent core is an absorbent sheet whose hydrophilic fibers are bonded together through a binder. Such an absorbent sheet is considerably stiff. Therefore, when the sanitary napkin is laterally compressed, the side regions can easily fold on the hinge lines without causing deformation in the vagina-facing region.

Also in the second aspect of the present invention, an upper absorbent core having a smaller area than the absorbent core (or lower absorbent core) may be disposed on a body surface of the lower absorbent core only within the vagina-facing region. The bending stiffness of the vagina-facing region can also be increased by securing the upper absorbent core on the lower absorbent core through an adhesive or by providing the compression portions.

In both the first and second aspect of the present invention, the side regions may have cuts penetrating through a thickness of the lower absorbent core or partway into the lower absorbent core or low-density portions where a density of the lower absorbent core is locally decreased. The side regions of the liquid-absorbent layer can be softened by providing the cuts or the low-density portions. Therefore, when the sanitary napkin is laterally compressed, the side regions can deform flexibly to fit against the crotch or the thighs. This also results in effectively preventing the vagina-facing region from being affected by such a compressive force.

In both the first and second aspect of the present invention, preferably, a cushion layer having a lower density than the absorbent core is disposed between the liquid-absorbent layer and the topsheet. The cushion layer can provide a comfortable feel against the crotch.

In both the first and second aspect of the present invention, compression portions where the liquid-absorbent layer is compressed and recessed together with the topsheet may lie on both sides of the longitudinal centerline and extend longitudinally of the sanitary napkin. According to a preferred embodiment, the hinge lines are located inside the compression portions. In this embodiment, since the hinge lines are located between side edges of the relatively stiff vagina-facing region and the relatively stiff compression portions, the liquid-absorbent layer can fold on the hinge lines more easily. Alternatively, the hinge lines may be located outside the compression portions.

BRIEF DESCRIPTION OF THE DRAWINGS

The present invention will be understood more fully from the detailed description given hereinafter and from the accompanying drawings of the preferred embodiment of the present invention, which, however, should not be taken to limit the invention, but are for explanation and understanding only.

In the drawings.

DESCRIPTION OF THE PREFERRED EMBODIMENT

The present invention will be discussed hereinafter in detail in terms of the preferred embodiment according to the present invention with reference to the accompanying drawings. In the following description, numerous specific details are set forth in order to provide a thorough understanding of the present invention. It will be obvious, however, to those skilled in the art that the present invention may be practiced without these specific details. In other instance, well-known structures are not shown in detail in order to avoid unnecessary obscuring of the present invention.

Figure 1:
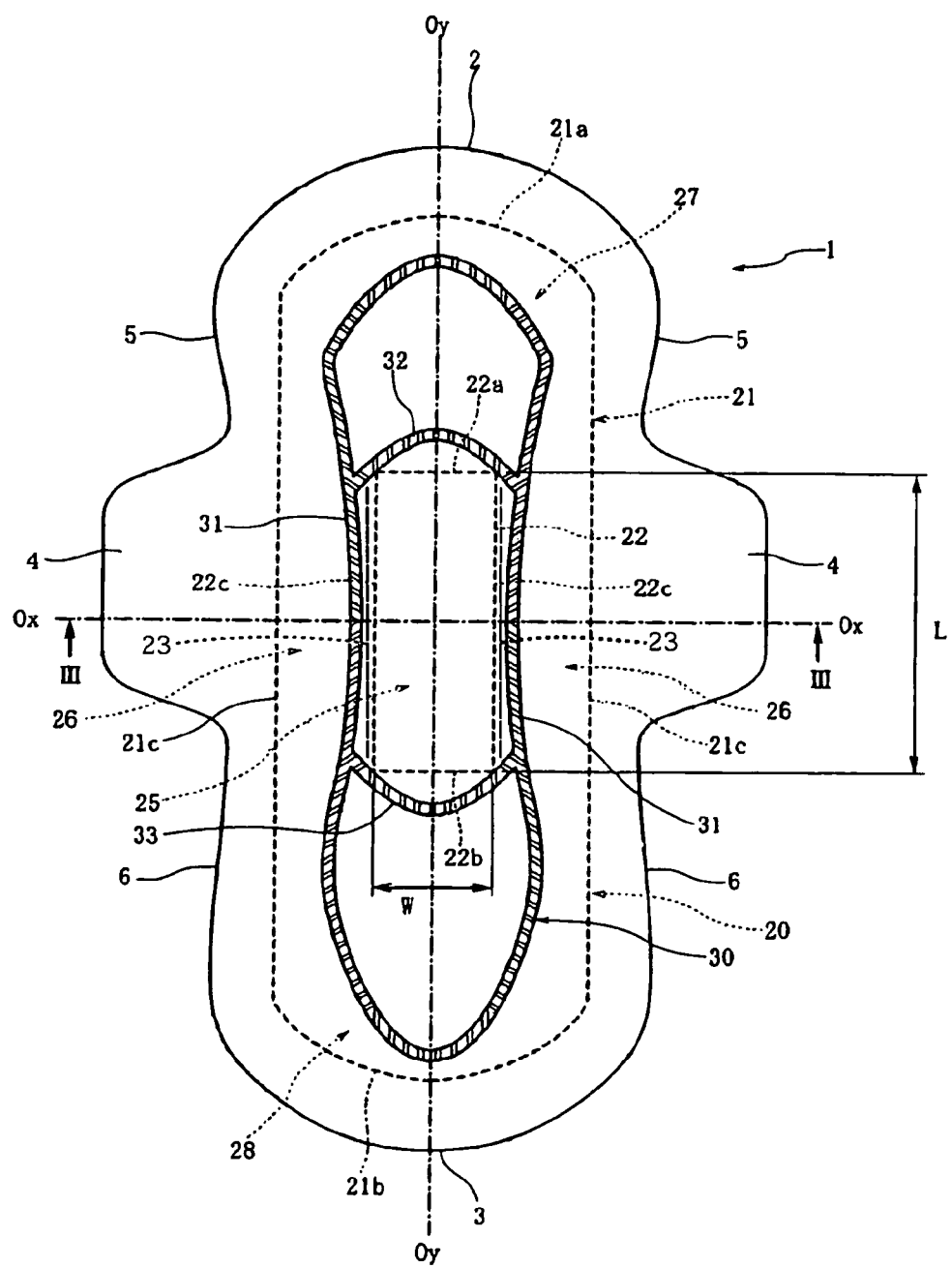
FIG. 1 is a plan view showing a body surface of a sanitary napkin according to a first embodiment of the present invention.
Figure 2:
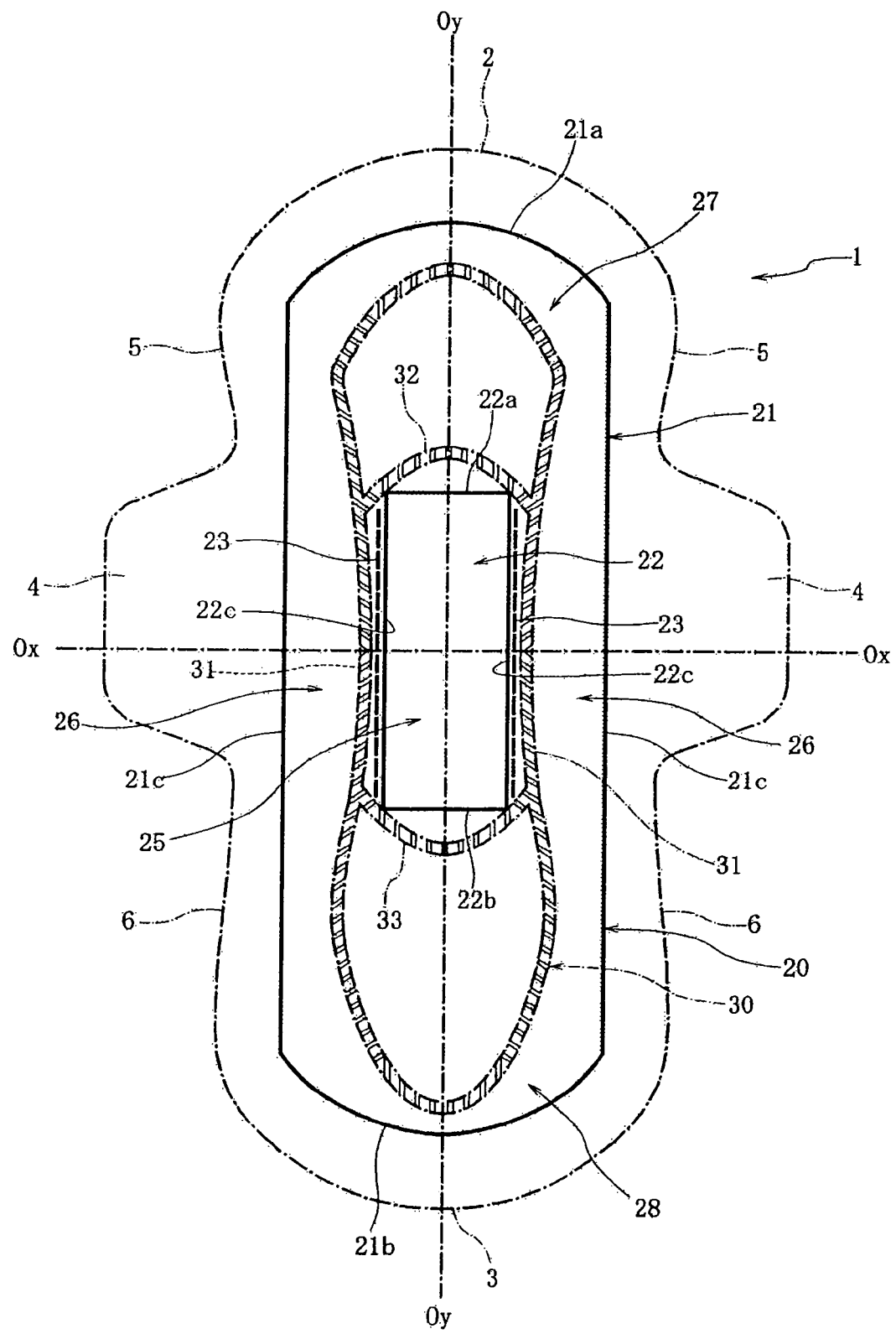
FIG. 2 is a plan view showing a liquid-absorbent layer in the context of the sanitary napkin of FIG. 1.
Figure 3A:
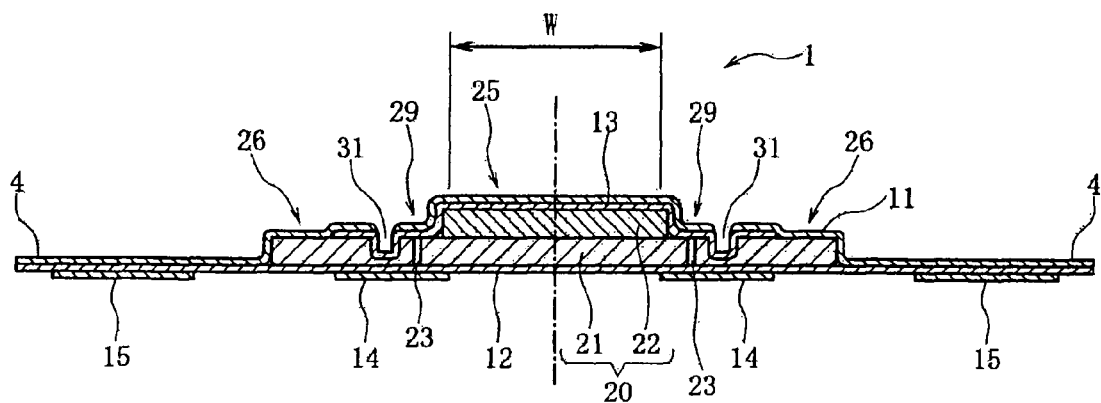
FIG. 3(A) is a sectional view of the sanitary napkin taken along line III-III of FIG. 1.
Figure 3B:
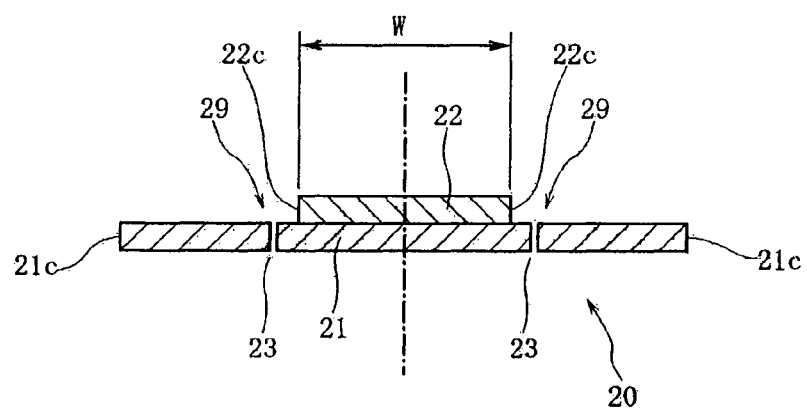
FIG. 3(B) is a sectional view of the liquid-absorbent layer.
Figure 4:
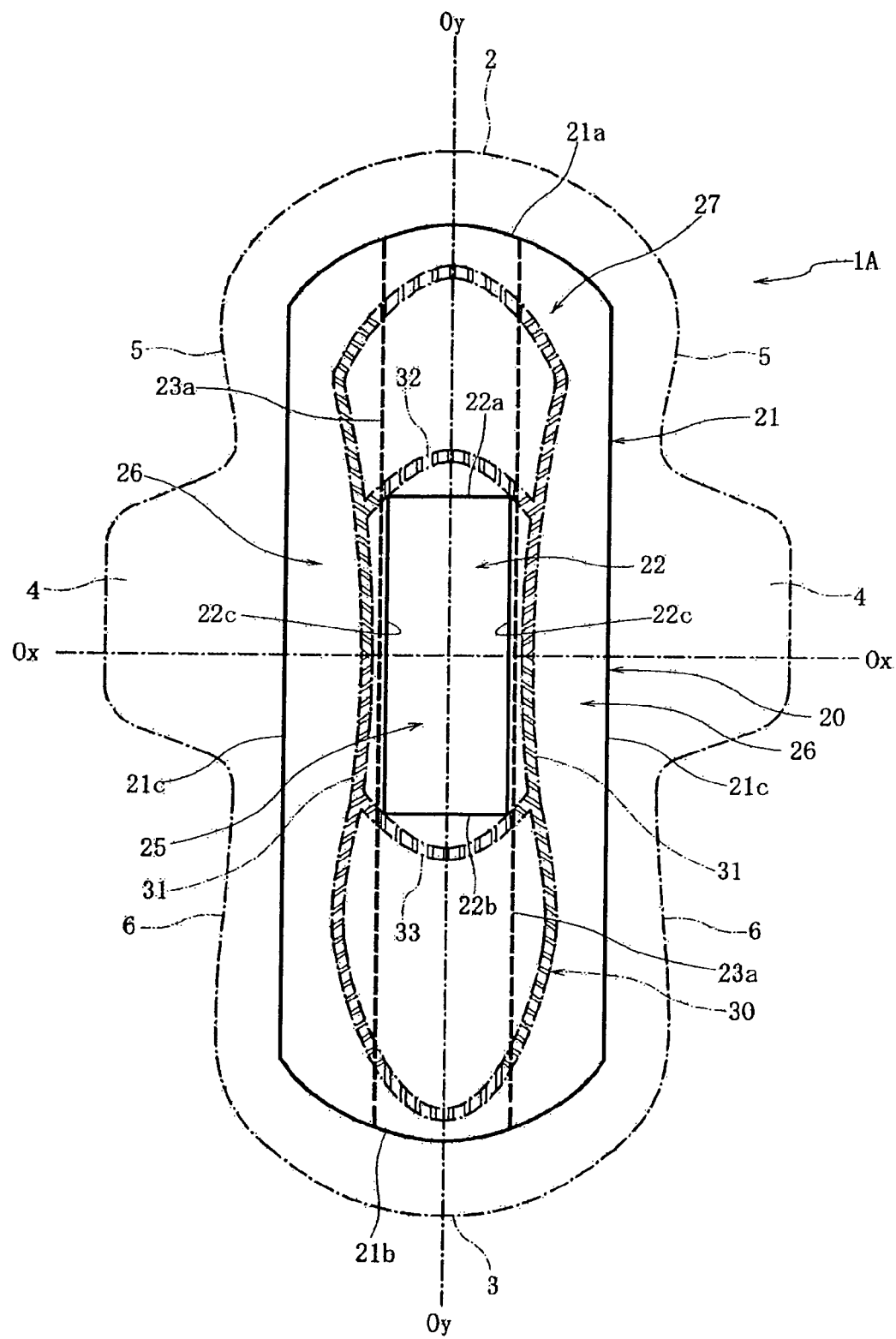
FIG. 4 is a plan view corresponding to FIG. 2, showing a modification of the first embodiment.
Figure 5:
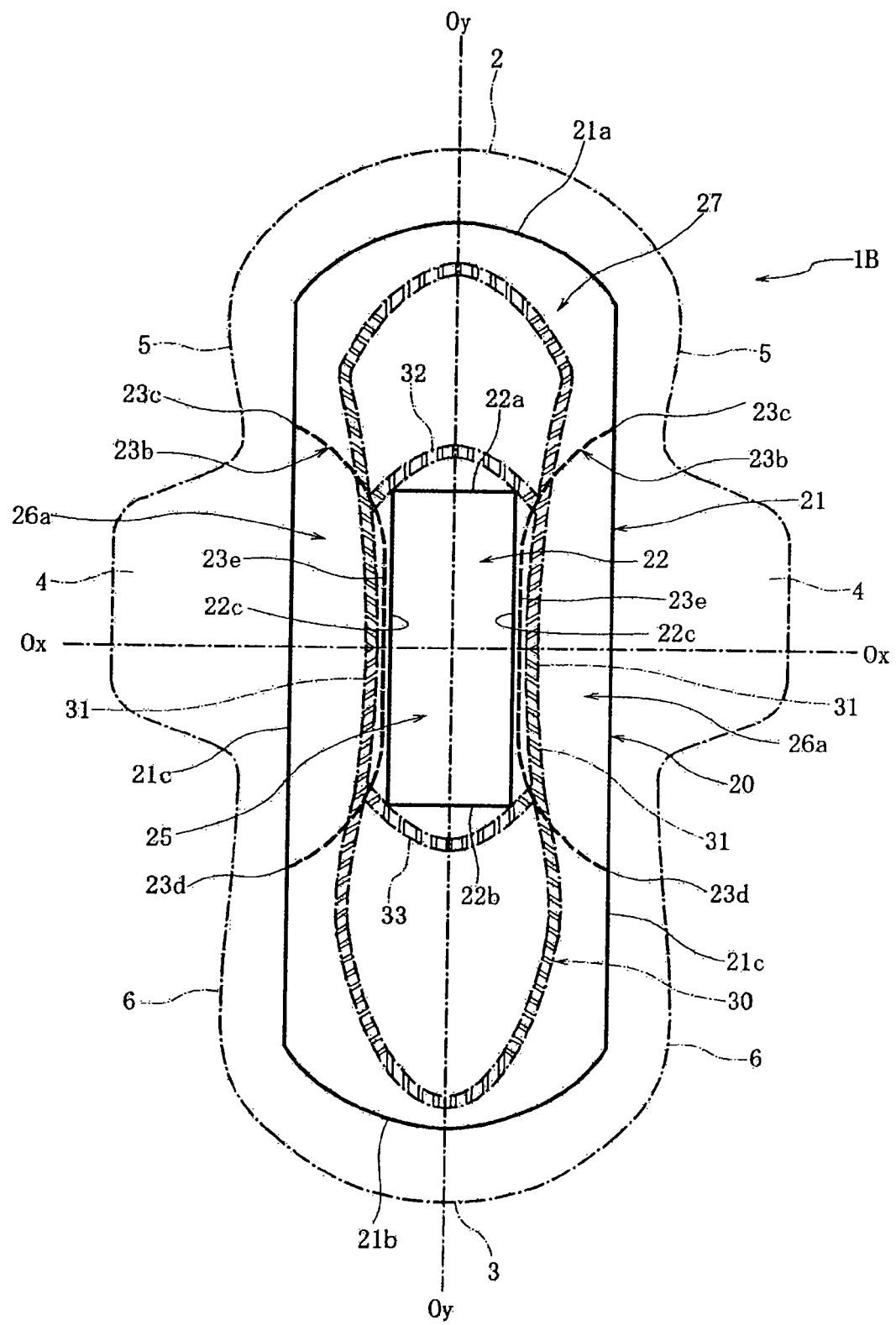
FIG. 5 is a plan view corresponding to FIG. 2, showing another modification of the first embodiment.

FIG. 1 is a plan view showing a body surface of a sanitary napkin 1 according to a first embodiment of the present invention, FIG. 2 is a plan view showing a liquid-absorbent layer contained in the sanitary napkin 1 of FIG. 1, FIG. 3(A) is a sectional view of the sanitary napkin 1 taken along line III-III of FIG. 1, FIG. 3(B) is a sectional view of the liquid-absorbent layer, and FIGS. 4 and 5 are plan views corresponding to FIG. 2, showing modifications of the first embodiment.

It should be noted that the sanitary napkin, as well as its individual components, has two major surfaces: of which one surface intended to be worn toward the wearer's crotch is referred to as "body surface", while the other surface is referred to as "garment surface". In addition, the lengthwise direction of the sanitary napkin is referred to as "longitudinal direction", while the direction perpendicular to the longitudinal direction is referred to as "lateral direction". With respect to dimensions of the individual components, unless otherwise stated, a dimension measured in the longitudinal direction is referred to as "length", while a dimension measured in the lateral direction is referred to as "width". Moreover, the term "inside" refers to one side closer to the center of the sanitary napkin, while the term "outside" refers to the other side away from the center of the sanitary napkin.

As shown in FIG. 1, the sanitary napkin 1 has arcuate front and rear edges 2, 3 and is elongated to have a length of about 180 to 450 mm as measured from the front edge 2 to the rear edge 3 on a longitudinal centerline Oy. On both right and left sides, the sanitary napkin 1 has laterally projecting fold-back flaps 4, 4. The sanitary napkin 1 has front side edges 5, 5 in front of the fold-back flaps 4, 4 and rear side edges 6, 6 behind the fold-back flaps 4, 4. In the sanitary napkin 1 shown in FIG. 1, the fold-back flaps 4, 4 are located closer to the front edge 2, so that the front side edges 5, 5 are somewhat shorter than the rear side edges 6, 6.

As shown in FIG. 3(A), the sanitary napkin 1 has a liquid-permeable topsheet 11 lying on the body surface side, a liquid-impermeable backsheet 12 lying on the garment surface side, and a liquid-absorbent layer 20 disposed between the topsheet 11 and the backsheet 12. Between the topsheet 11 and the liquid-absorbent layer 20, furthermore, there is provided a cushion layer 13 having a lower fiber density than the liquid-absorbent layer 20.

On the garment surface of the backsheet 12, there are provided a plurality of pressure-sensitive adhesive layers 14. The pressure-sensitive adhesive layers 14 may be in the form of a strip which extends in parallel to the longitudinal centerline Oy beneath the liquid-absorbent layer 20. Also in the fold-back flaps 4, pressure-sensitive adhesive layers 15 are provided on the garment surface of the backsheet 12. These pressure-sensitive adhesive layers 15 may be in a rectangular form.

When the sanitary napkin 1 is applied to the wearer's body, the pressure-sensitive adhesive layers 14 are adhered to an inner side of a crotch part of an undergarment. Subsequently, the fold-back flaps 4 are folded back against an outer side of the crotch part of the undergarment along side edges of the crotch part and adhered thereto through the pressure-sensitive adhesive layers 15.

The liquid-absorbent layer 20 is constructed of a lower absorbent core 21 and an upper absorbent core 22. The lower absorbent core 21 has a smaller contour than the sanitary napkin 1. As shown in FIGS. 1 and 2, the lower absorbent core 21 has arcuate front and rear edges 21a, 21b. The front edge 21a is located behind the front edge 2 of the sanitary napkin 1; the rear edge 21b is located forward of the rear edge 3 of the sanitary napkin 1. The lower absorbent core 21 has straight side edges 21c, 21c in parallel to the longitudinal centerline Oy. The side edges 21c, 21c of the lower absorbent core 21 are located inside the front side edges 5, 5 and the rear side edges 6, 6 of the sanitary napkin 1.

The topsheet 11 and the backsheet 12 have the same contour as the sanitary napkin 1 and may be bonded to each other through a hot-melt type adhesive outside the front edge 21a, the rear edge 21b, and the side edges 21c, 21c of the lower absorbent core 21.

The upper absorbent core 22 has a smaller area than the lower absorbent core 21. As shown in FIGS. 1 and 2, the upper absorbent core 22 is rectangular and has straight front and rear edges 22a, 22b and straight side edges 22c, 22c. The side edges 22c, 22c are in parallel to the longitudinal centerline Oy.

The upper absorbent core 22 may have a length L in the range of 60 to 140 mm and a width W in the range of 15 to 40 mm.

Of the liquid-absorbent layer 20, the area where the upper absorbent core 22 is laid on the lower absorbent core 21 (i.e., the area of L×W) is vagina-facing region 25; the areas defined between the side edges 22c of the upper absorbent core 22 and the side edges 21c of the lower absorbent core 21 are side regions 26, 26; the area lying in front of the front edge 22a of the upper absorbent core 22 is front region 27; and the area lying behind the rear edge 22b of the upper absorbent core 22 is rear region 28. The liquid-absorbent layer 20 of the first embodiment has only the lower absorbent core 22 in the side regions 26, the front region 27, and the rear region 28.

The lower and upper absorbent cores 21, 22 are absorbent sheets manufactured by bonding hydrophilic fibers through a binder. These absorbent sheets may be air-laid pulp comprising 50-80% by weight of fluff pulp (or comminuted pulp), 10-40% by weight of superabsorbent polymer (SAP), and 5-20% by weight of binder such as ethylene-vinyl acetate copolymer. The air-laid pulp may be manufactured by depositing the fluff pulp into a fibrous web by air-laid process, distributing the SAP over the fibrous web, spraying the binder, and heating and pressing the fibrous web.

It is preferred without limitation that the lower absorbent core 21 has a basis weight in the range of 80 to 400 g/m$^2$ and the upper absorbent core 22 has a basis weight in the range of 80 to 200 g/m$^2$. The individual absorbent cores 21, 22 may be made of a single piece of the absorbent sheet or a laminate of two or more pieces of the absorbent sheet, which are bonded to each other through a hot-melt type adhesive applied in such an amount as not to interfere with passage of liquid. If desired, another layer of hydrophilic fibers, such as a fluff pulp layer without containing binder, may be laid on the absorbent sheet as long as the resulting absorbent core has proper bending stiffness.

The lower and upper absorbent cores 21, 22 may be bonded to each other through a hot-melt type adhesive applied in such an amount as not to interfere with passage of liquid. The vagina-facing region 25 has a greater bending stiffness than the side regions 26, the front region 27, and the rear region 28, because the lower and upper absorbent cores 21, 22 are bonded to each other in the vagina-facing region 25.

The vagina-facing region 25 where the lower and upper absorbent cores 21, 22 are bonded to each other, preferably has a Gurley stiffness of at least 3.92 mN (400 mgf). A difference in Gurley stiffness between the vagina-facing region 25 and the side regions 26 only of the lower absorbent core 21 is preferably at least 1.96 mN (200 mgf), more preferably at least 2.94 mN (300 mgf). Although not particularly limited, the lower limit of the Gurley stiffness of the side regions 26 is preferably about 0.392 mN (40 mgf).

When thus constructed, the stiffness difference between vagina-facing region 25 and the side regions 26 provides hinge lines 29 slightly outside the side edges 22c of the upper absorbent core 22. The hinge line 29 is a line on which the side region 26 can easily fold.

In the first embodiment, furthermore, cuts (through-holes) 23 are made in the lower absorbent core 21 along the hinge line 29. As shown in FIG. 3(B), the cuts 23 penetrate through the lower absorbent core 21 from one side to the other. As shown in FIG. 2, the cuts 23 are short cuts arranged linearly at intervals in the longitudinal direction. In other words, the cuts 23 are arranged in the form of a perforation (or dashed line).

As shown in FIG. 2, the cuts 23 are arranged to extend almost the entire length of the side edges 22c. Providing the cuts 23 further facilitates folding of the side regions 26 along the hinge lines 29. In the first embodiment, therefore, the hinge lines 29 are provided not only by the stiffness difference between the vagina-facing region 25 and the side regions 26 but also by providing the cuts 23.

On the other hand, even when the side regions 26 fold on the hinge lines 29 due to pressure laterally exerted on the sanitary napkin 1, the vagina-facing region 25, which is constructed of the lower and upper absorbent cores 21, 22 to increase the bending stiffness, is resistant to folding. Thus, the vagina-facing region 25 can be applied to the crotch while being kept in a relatively flat state.

The cuts 23 arranged along the hinge lines 29 are not required to extend the entire length of the side edges 22c of the upper absorbent core 22, but may extend shorter than the length of the side edges 22c. The cuts 23 arranged in the form of a perforation (or dashed line) may be replaced by a single slit or groove extending continuously in the longitudinal direction.

The cuts 23 may penetrate partway into the lower absorbent core 21 without penetrating through the thickness of the lower absorbent core 21. If desired, the individual cuts 23 may be in the form of a bore having a circular opening and penetrating through the thickness of the lower absorbent core 21 or partway into the lower absorbent core 21. Such bores may be provided by needling the lower absorbent core 21.

Alternatively, the density of the lower absorbent core 21 may be locally decreased along the hinge lines 29. Such a low-density portion may be provided by locally stretching the lower absorbent core 21 in the lateral direction.

In the first embodiment, as set forth above, the hinge lines 29 are provided not only by the stiffness difference between the vagina-facing region 25 and the side regions 26 but also by providing the cuts 23. However, the present invention should not be construed as limited to the first embodiment. For example, the hinge lines 29 may be provided without providing the cuts 23, as long as the difference in Gurley stiffness between the vagina-facing region 25 and the side regions 26 is at least 1.96 mN (200 mgf) and preferably at least 2.94 mN (300 mgf). If the cuts 23 are provided as in the first embodiment, the difference in Gurley stiffness between the vagina-facing region 25 and the side regions 26 may be smaller than the above range.

The sanitary napkin 1 has a compression line 30 on the body surface. As shown in FIG. 1, the compression line 30 includes: an outer compression line 31 which surrounds an elongated area lying on the lower absorbent core 21; a front inner compression line 32 which is curved to protrude forward near the front edge 22a of the upper absorbent core 22; and a rear inner compression line 33 which is curved to protrude rearward near the rear edge 22b of the upper absorbent core 22. In the first embodiment, the compression line 30 does not overlap with the upper absorbent core 22.

The compression line 30 may be formed by heating and pressing the topsheet 11, the cushion layer 13, and the lower absorbent core 21, as shown in FIG. 3(A). The compression line 30 takes the form of a groove which is formed in the body surface of the sanitary napkin 1. At the compression line 30, the lower absorbent core 21 is compressed to have a greater density than the remaining portions. The cushion layer 13, which should be at least as large as to cover the upper absorbent core 22, is not necessarily required to extend to the compression line 30.

As shown in FIG. 2, the cuts 23 made in the lower absorbent core 21 lie between the side edges 22c of the upper absorbent core 22 and the outer compression line 31. Since the cuts 23 are located between the vagina-facing region 25 where stiffness is increased by lamination and the outer compression line 31 where stiffness is increased by compression, the liquid-absorbent layer 20 can easily fold on the cuts 23.

As shown in FIG. 1, the distance between laterally opposing portions of the compression line 31 becomes a minimum at a midpoint between the front and rear inner compression lines 32, 33. In FIG. 1, a lateral reference line which is an imaginary line extending laterally and coinciding with the location where the distance between the laterally opposing portions of the compression line 31 becomes a minimum, is indicated by Ox. The lateral reference line Ox almost coincides with the midpoint of the length L of the upper absorbent core 22. The sanitary napkin 1 can be put on following the contour of the compression line 31 such that the intersection of the lateral reference line Ox and the longitudinal centerline Oy may coincide with the center of the vaginal opening.

The topsheet 11 may be a through-air bonded nonwoven fabric having a basis weight of about 10 to 50 g/m$^2$. Constituent fibers of the through-air bonded nonwoven fabric may be polyethylene/polyethylene terephthalate sheath/core bicomponent fibers with an inorganic filler such as titanium oxide mixed into the core of polyethylene terephthalate. The topsheet 11 may be made of other materials as long as the topsheet 11 is permeable to liquid. For example, there may be used a point-bonded nonwoven fabric, a spunlaced nonwoven fabric, or a spunbonded nonwoven fabric. Alternatively, there may be used a resin film with a large number of apertures for passage of liquid.

The backsheet 12 may be a film such as a polyethylene film, and is preferably permeable to moisture.

For the cushion layer 13, there may be used a through-air bonded nonwoven fabric. For example, the through-air bonded nonwoven fabric may be made of eccentric sheath/core bicomponent fibers of which the core is polypropylene and the sheath is polyethylene. The through-air bonded nonwoven fabric may have a basis weight of about 20 g/m$^2$ and be folded in four for use as the cushion layer 13. The cushion layer 13 may have a fluff pulp layer wrapped in a tissue beneath the through-air bonded nonwoven fabric. Alternatively, the cushion layer 13 may be the fluff pulp layer alone.

Since the relatively stiff vagina-facing region 25 has the cushion layer 13 on the upper absorbent core 22, the vagina-facing region 25 provides a comfortable feel against the vaginal opening.

Figure 13:
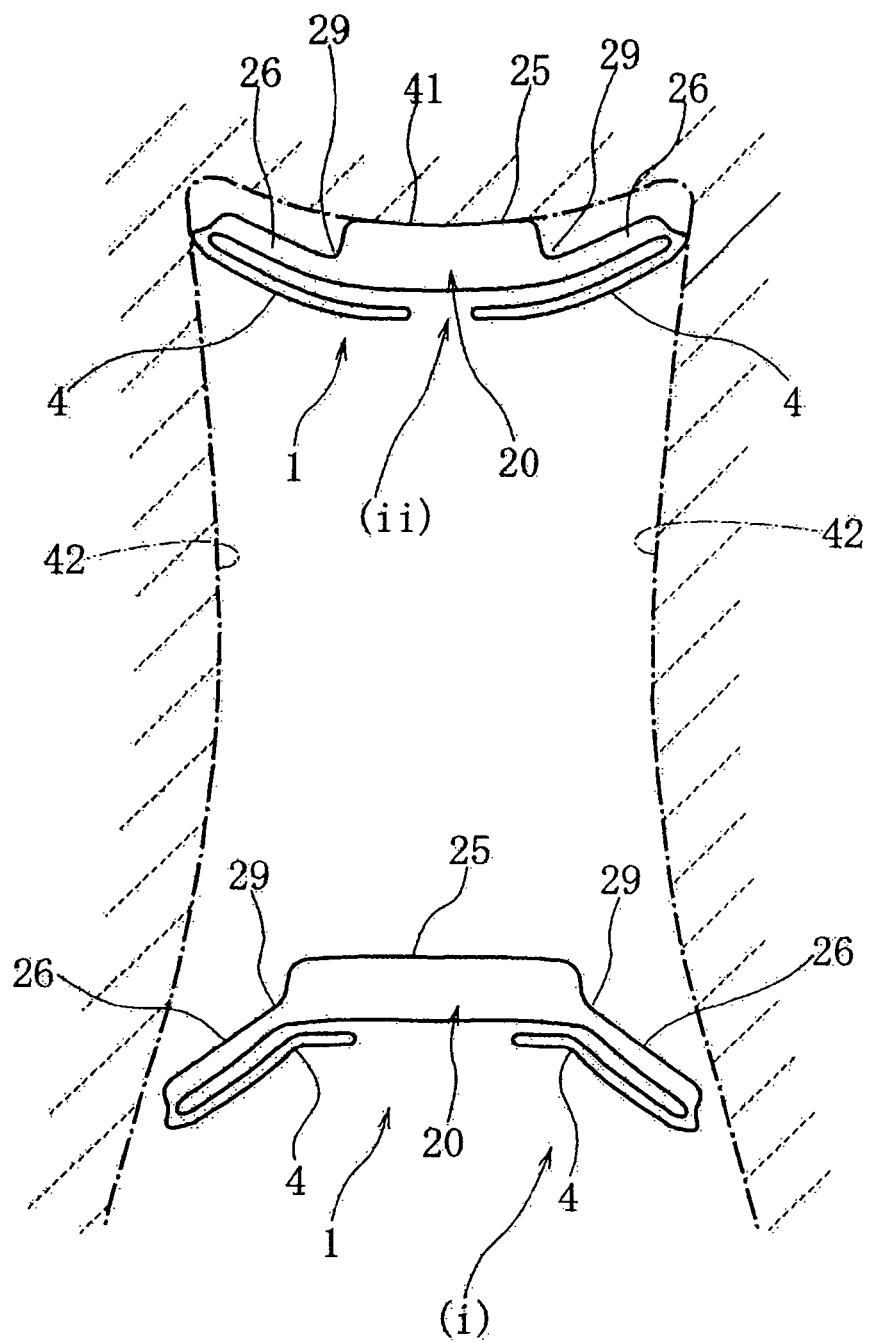
FIG. 13 is a schematic diagram explaining how a sanitary napkin will be deformed when an undergarment is pulled up.

FIG. 13 is a schematic diagram explaining how the sanitary napkin 1 will be deformed when the undergarment is pulled up toward the crotch of a woman's body. In FIG. 13, the crotch is indicated by 41 and the thighs are indicated by 42. Although the sanitary napkin 1 should be worn while being fixed on the crotch part of the undergarment, the undergarment is omitted in FIG. 13 for clarity.

When putting on the sanitary napkin 1, the pressure-sensitive adhesive layers 14 are adhered to the inner side of the crotch part of the undergarment. Subsequently, the fold-back flaps 4 are folded back against the outer side of the crotch part of the undergarment along the side edges of the crotch part and adhered thereto through the pressure-sensitive adhesive layers 15. In general, the sanitary napkin 1 is positioned on the undergarment after the wearer's legs are inserted into leg openings of the undergarment.

When the sanitary napkin 1 is at a position (i) shown in FIG. 13 on the way to the crotch 41, the thighs 42 exert lateral compressive force on the side regions 26 of the liquid-absorbent layer 20 or the sanitary napkin 1 is centrally pulled upward by the crotch part of the undergarment. This tries to make the sanitary napkin 1 bulge toward the crotch 41 at the longitudinal centerline Oy.

However, the liquid-absorbent layer 20 is relatively stiff in the vagina-facing region 25 and has the hinge lines 29 on which the side regions 26 can easily fold. At the position (i), therefore, the side regions 26 are folded by the external force, preventing too much deformation of the relatively stiff vagina-facing region 25. Thus, the vagina-facing region 25 can migrate to the crotch 41 while being kept in an almost flat, undeformed state.

At a position (ii) shown in FIG. 13, the vagina-facing region 25 comes into contact with the vaginal opening in such an almost flat, undeformed state. Therefore, the vagina-facing region 25 can closely fit against the vaginal opening, which ensures that menstrual blood passes through the cushion layer 13 and is absorbed by the liquid-absorbent layer 20 due to liquid absorbing force of the upper absorbent core 22. At the position (ii), furthermore, the side regions 26, which are allowed to freely fold on the hinge lines 29, can easily fit against the crotch 41 or the thighs 42, which ensures that menstrual blood trying to flow laterally is absorbed by the lower absorbent core 21 in the side regions 26 and prevented from leaking laterally.

Next, there will be described sanitary napkins as modifications of the first embodiment and sanitary napkins according to other embodiments. Hereinbelow, the detailed description of the portions having the same construction and shape as those of the sanitary napkin 1 will be omitted by designating them by the common reference numerals.

FIGS. 4 and 5 show sanitary napkins 1A and 1B which are modifications of the sanitary napkin 1 according to the first embodiment. The sanitary napkins 1A and 1B are different from the sanitary napkin 1 only in arrangement of cuts made in the lower absorbent core 21.

In the sanitary napkin 1A shown in FIG. 4, the lower absorbent core 21 has cuts 23a that are arranged to extend longer than the length of the side edges 22c of the upper absorbent core 22. More specifically, the cuts 23a, which are arranged on both sides of the longitudinal centerline Oy and in parallel to the longitudinal centerline Oy, extend over the length of the lower absorbent core 21 from the front edge 21a to the rear edge 21b. Some of the cuts 23a lie between the side edges 22c of the upper absorbent core 22 and the outer compression line 31.

In the sanitary napkin 1A, the hinge lines 29 of the cuts 23a extend over the length of the lower absorbent core 21 to facilitate folding of the areas defined between the cuts 23a and the side edges 21c. However, the hinge lines 29 of the cuts 23a are not required to extend to the front edge 21a and the rear edge 21b of the lower absorbent core 21, but may terminate between the front edge 22a of the upper absorbent core 22 and the front edge 21a of the lower absorbent core 21 and between the rear edge 22b of the upper absorbent core 22 and the rear edge 21b of the lower absorbent core 21.

In the sanitary napkin 1B shown in FIG. 5, the lower absorbent core 21 has cuts 23b that are arranged in a curved line on both sides of the longitudinal centerline Oy. The curved line of the cuts 23b has front and rear ends 23c, 23d on the side edge 21c of the lower absorbent core 21 with its intermediate portion located closer to the longitudinal centerline Oy.

This intermediate portion extends straight substantially in parallel to the longitudinal centerline Oy and is called straight portion 23e. The straight portions 23e lie between the side edges 22c of the upper absorbent core 22 and the outer compression line 31. These straight portions 23e are preferably at least ⅓, more preferably at least ½ the length L of the side edges 22c of the upper absorbent core 22.

In the sanitary napkin 1B shown in FIG. 5, the areas defined between the side edges 21c of the lower absorbent core 21 and the curved lines of the cuts 23b are side regions 26a. The side regions 26a lie on both sides of the vagina-facing region 25 where the upper absorbent core 22 is secured on the lower absorbent core 21 through an adhesive.

In the sanitary napkin 1B, the curved lines of the cuts 23b facilitate deformation of the side regions 26a in conformity with the contour of the thighs. Furthermore, the straight portions 23e lying between the side edges 22c of the upper absorbent core 22 and the outer compression line 31 facilitate folding of the side regions 26a.

Figure 6:
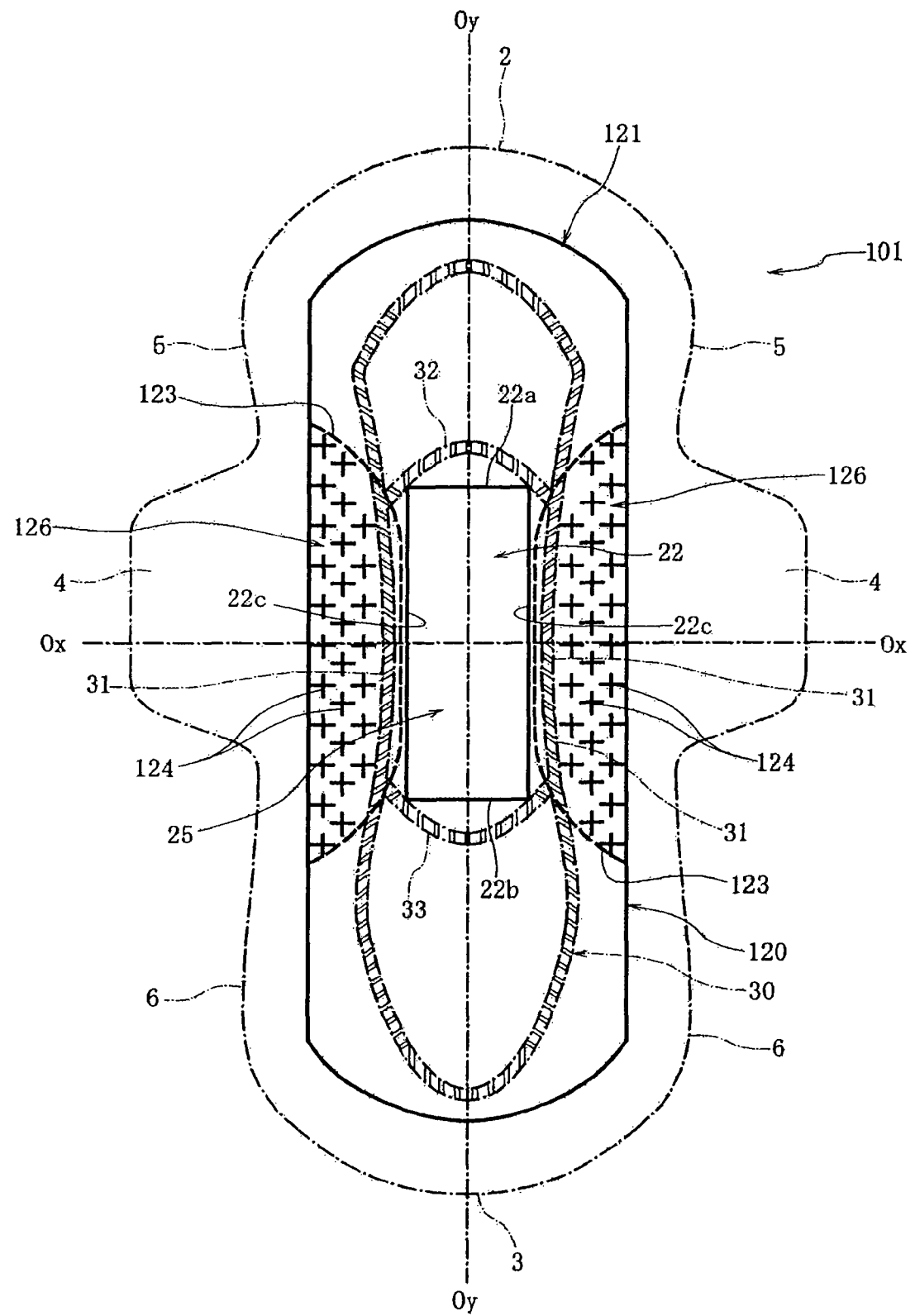
FIG. 6 is a plan view showing a liquid-absorbent layer in the context of a sanitary napkin according to a second embodiment of the present invention.

FIG. 6 is a plan view corresponding to FIG. 2 and showing a liquid-absorbent layer 120 contained in a sanitary napkin 101 according to a second embodiment of the present invention.

The liquid-absorbent layer 120 is constructed of a lower absorbent core 121 and the upper absorbent core 22. The lower absorbent core 121 is made of the same material as the lower absorbent core 21 of the first embodiment. That is, the lower absorbent core 121 is an absorbent sheet manufactured by bonding hydrophilic fibers through a binder (e.g., air-laid pulp). The lower absorbent core 121 has the same plan view contour as the lower absorbent core 21. The upper absorbent core 22 is the same as used for the sanitary napkin 1 of the first embodiment. The upper absorbent core 22 is secured on the lower absorbent core 121 through an adhesive to provide the vagina-facing region 25.

The lower absorbent core 121 has cuts 123 that are arranged in the same manner as the cuts 23b of the sanitary napkin 1B shown in FIG. 5. That is, the cuts 123 are arranged in a curved line with its intermediate straight portion located closer to the longitudinal centerline Oy and between the side edges 22c of the upper absorbent core 22 and the outer compression line 31. The cuts 123 define side regions 126.

In the side regions 126, the lower absorbent core 121 is softened. In the embodiment shown in FIG. 6, a number of cuts 124 are made in the lower absorbent core 121 within the side regions 126. The cuts 124 penetrate through the thickness of the lower absorbent core 121. The individual cuts 124 are formed of two straight cuts crossing each other. As with the cuts 23, 23a, 23b, 123 made along the hinge lines 29, if desired, the lower absorbent core 121 may be cut partway through the thickness to provide the cuts 124 for softening.

The cuts 124 should not be understood as limited to the pattern shown in FIG. 6. For example, a number of longitudinally extending short straight cuts may be arranged in a given pattern. Alternatively, a number of bores having a circular opening may penetrate through the thickness of the lower absorbent core 121 or partway into the lower absorbent core 121.

Softening the side regions 126 of the liquid-absorbent layer 120 facilitates deformation of the lower absorbent core 121 in the side regions 126.

Accordingly, the side regions 126 can easily be deformed when the sanitary napkin 101 is laterally compressed by the thighs 42 at the position (i) shown in FIG. 13, which effectively prevents deformation of the vagina-facing region 25. At the position (ii) shown in FIG. 13, furthermore, since the side regions 126 can easily be deformed by an external force exerted on the sanitary napkin 101, the vagina-facing region 25 is effectively prevented from being affected by a deforming force to ensure contact with the vaginal opening. Moreover, the soft side regions 126, which can easily fit against the crotch 41 or the thighs 42, ensure that menstrual blood flowing to the side regions 126 is absorbed by the lower absorbent core 121.

It should be noted that the side regions may be softened also in the sanitary napkin 1 shown in FIGS. 1 to 3 and the sanitary napkin 1A shown in FIG. 4.

Figure 7:
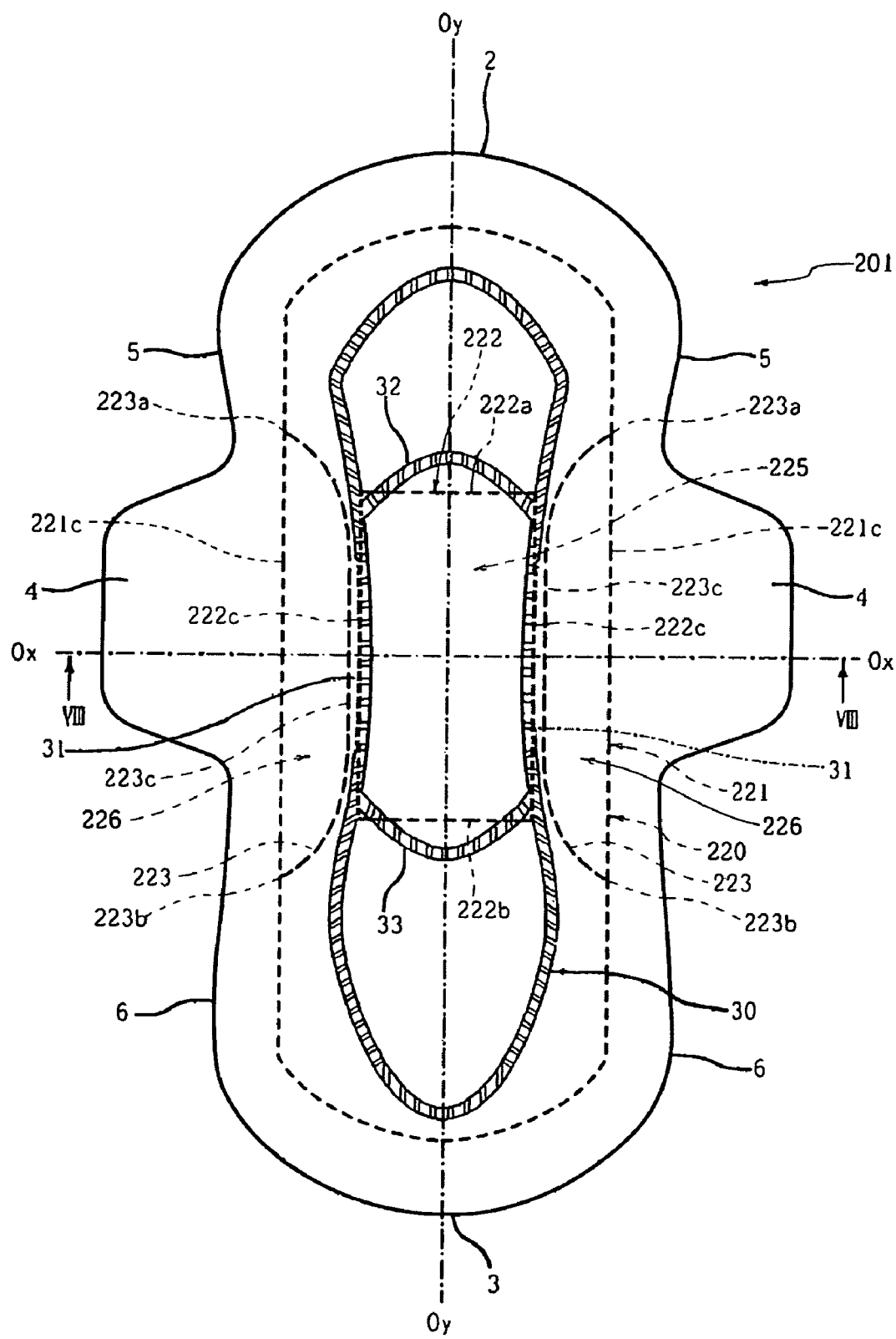
FIG. 7 is a plan view showing a body surface of a sanitary napkin and a liquid-absorbent layer in the context of the sanitary napkin according to a third embodiment of the present invention.
Figure 8:
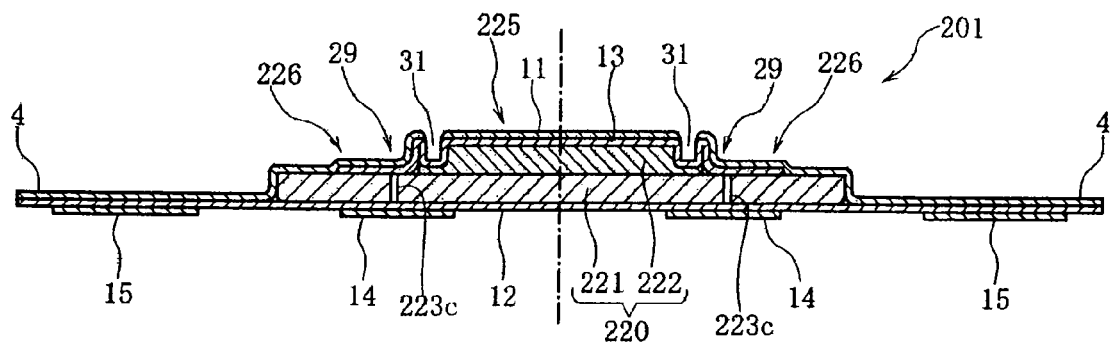
FIG. 8 is a sectional view taken along line VIII-VIII of FIG. 7.

FIG. 7 is a plan view corresponding to FIG. 1 and showing a body surface of a sanitary napkin and a liquid-absorbent layer 220 contained in the sanitary napkin 201 according to a third embodiment of the present invention. FIG. 8 is a sectional view of the sanitary napkin 201 take along line VIII-VIII of FIG. 7.

The liquid-absorbent layer 220 is constructed of a lower absorbent core 221 and an upper absorbent core 222. The lower and upper absorbent cores 221, 222 are similar to the lower and upper absorbent cores 21, 22 shown in FIGS. 1 to 3. That is, the lower and upper absorbent cores 221, 222 are absorbent sheets manufactured by bonding hydrophilic fibers through a binder (e.g., air-laid pulp).

As shown in FIG. 7, the upper absorbent core 222 is rectangular and has a straight front edge 222a, a straight rear edge 222b, and straight side edges 222c, 222c. This upper absorbent core 222 has a larger width than the upper absorbent core 22 shown in FIGS. 1 to 6 with the side edges 222c, 222c located on or outside the outer compression line 31. Accordingly, a part of the outer compression line 31 is formed by compressing the topsheet 11, the cushion layer 13, the upper absorbent core 222, and the lower absorbent core 221, as shown in FIG. 8.

Since both the upper and lower absorbent cores 222, 221 are compressed at the outer compression line 31, the upper absorbent core 222 can be secured on the lower absorbent core 221 without applying an adhesive between the upper and lower absorbent cores 222, 221. Thus, the bending stiffness of a vagina-facing region 225 can be increased as in the embodiments where the upper and lower absorbent cores are secured through an adhesive.

The lower absorbent core 221 has cuts 223 which provide the hinge lines 29 on both sides thereof. Like the cuts 23 shown in FIG. 5, the cuts 223 are arranged in a curved line with its intermediate portion located closer to the longitudinal centerline Oy. The curved line of the cuts 223 has front and rear ends 223a, 223b on the side edge 221c of the lower absorbent core 221. The intermediate portion extends straight and is called straight portion 223c. The straight portions 223c lie outside the outer compression line 31. The straight portions 223c extend almost the entire length of the side edges 222c of the upper absorbent core 222 in parallel to the longitudinal centerline Oy.

In the sanitary napkin 201, the area where the upper absorbent core 222 lies is the vagina-facing region 225, while the areas defined between the side edges 221c of the lower absorbent core 221 and the cuts 223 are side regions 226.

The stiffness of the vagina-facing region 225 is locally increased at both side portions where the lower and upper absorbent cores 221, 222 are compressed to provide the outer compression line 31. Since the straight portions 223c of the cuts 223 lie immediately outside the side portions where the stiffness is locally increased, the lower absorbent core 221 can easily fold on the straight portions 223c of the cuts 223 due to the stiffness difference.

Figure 9:
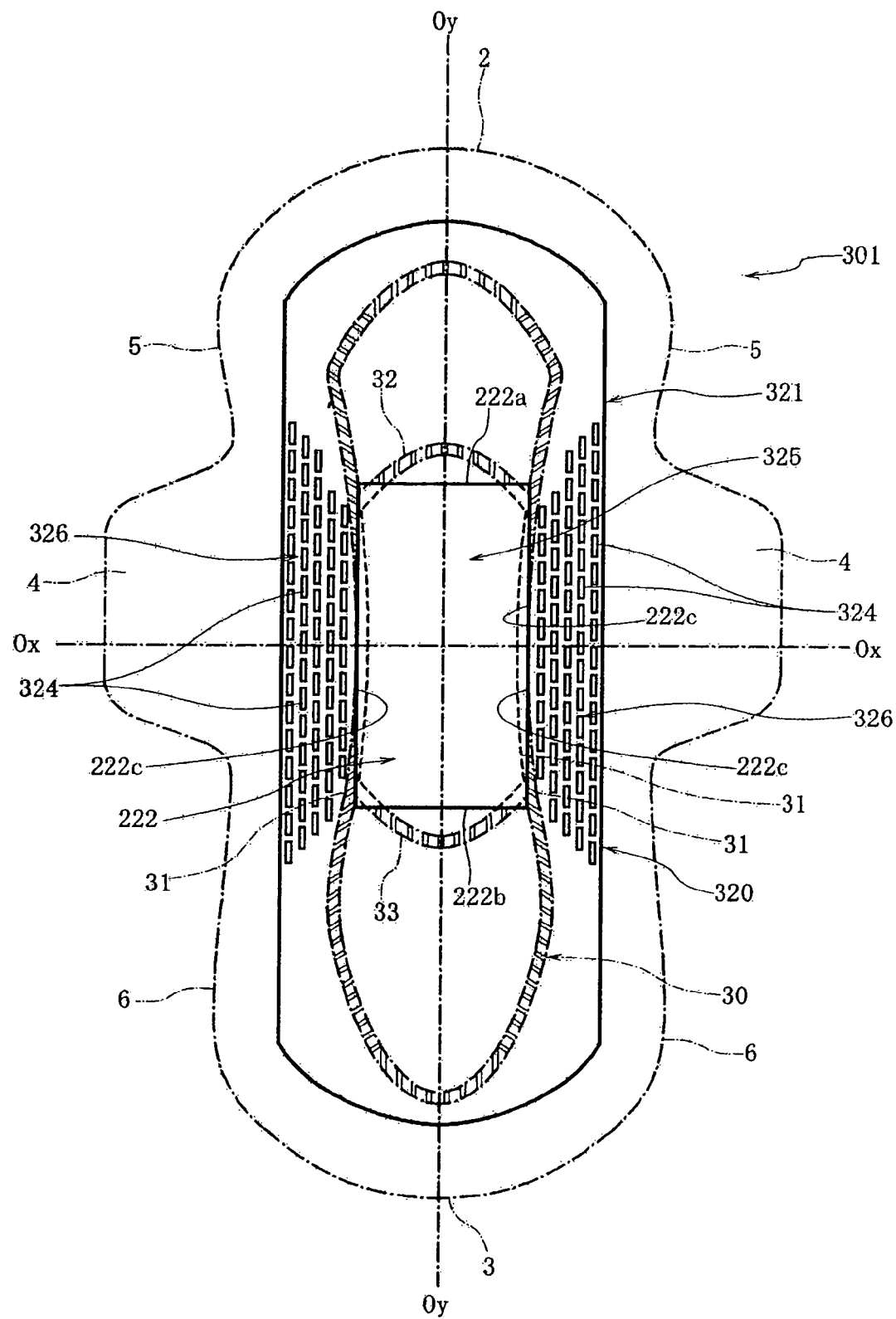
FIG. 9 is a plan view showing a liquid-absorbent layer in the context of a sanitary napkin according to a fourth embodiment of the present invention.

FIG. 9 is a plan view corresponding to FIG. 2 and showing a liquid-absorbent layer 320 contained in a sanitary napkin 301 according to a fourth embodiment of the present invention.

The liquid-absorbent layer 320 is constructed of a lower absorbent core 321 and the upper absorbent core 222. The upper absorbent core 222 is the same as used for the sanitary napkin 201 shown in FIG. 7. The upper absorbent core 222 is laid on the body surface of the lower absorbent core 321, and the outer compression line 31 is formed in the side portions of the upper absorbent core 222, thereby securing the upper absorbent core 222 on the lower absorbent core 321.

The area where the upper absorbent core 222 lies is vagina-facing region 325. On both sides of the upper absorbent core 222, the lower absorbent core 321 is softened. The softening is carried out by forming a plurality of low-density portions 324 in the lower absorbent core 321. For example, the softening may be carried out by processing a part of the absorbent sheet (e.g., air-laid pulp) at room temperature between meshing rolls with a plurality of projections (or teeth). The projections locally exert a tension on the absorbent sheet to locally decrease the density of the absorbent sheet, which provides the low-density portions 324 in accordance with the pattern of the projections.

In the liquid-absorbent layer 320 shown in FIG. 9, it should be noted that the lower absorbent core 321 is not formed with the cuts 223 shown in FIG. 7, but the boundaries between the softened areas of the low-density portions 324 and the remaining area extend in a curved line with its intermediate portion located closer to the longitudinal centerline Oy.

In the sanitary napkin 301, the vagina-facing region 325 where the upper absorbent core 222 is laid on the lower absorbent core 321 has a greater stiffness than side regions 326 formed with the low-density portions 324. Therefore, hinge lines on which the side regions 326 can easily fold are provided near the side edges 222c of the upper absorbent core 222. Furthermore, the softened side regions 326 can easily be deformed by an external force.

In the sanitary napkin 301 shown in FIG. 9, the side regions 326 may be formed with the cuts 124 shown in FIG. 6, in place of the low-density portions 324. If desired, the low-density portions 324 may be formed in the foregoing embodiments and the modifications shown in FIGS. 1 to 8 to soften the side regions.

Figure 10:
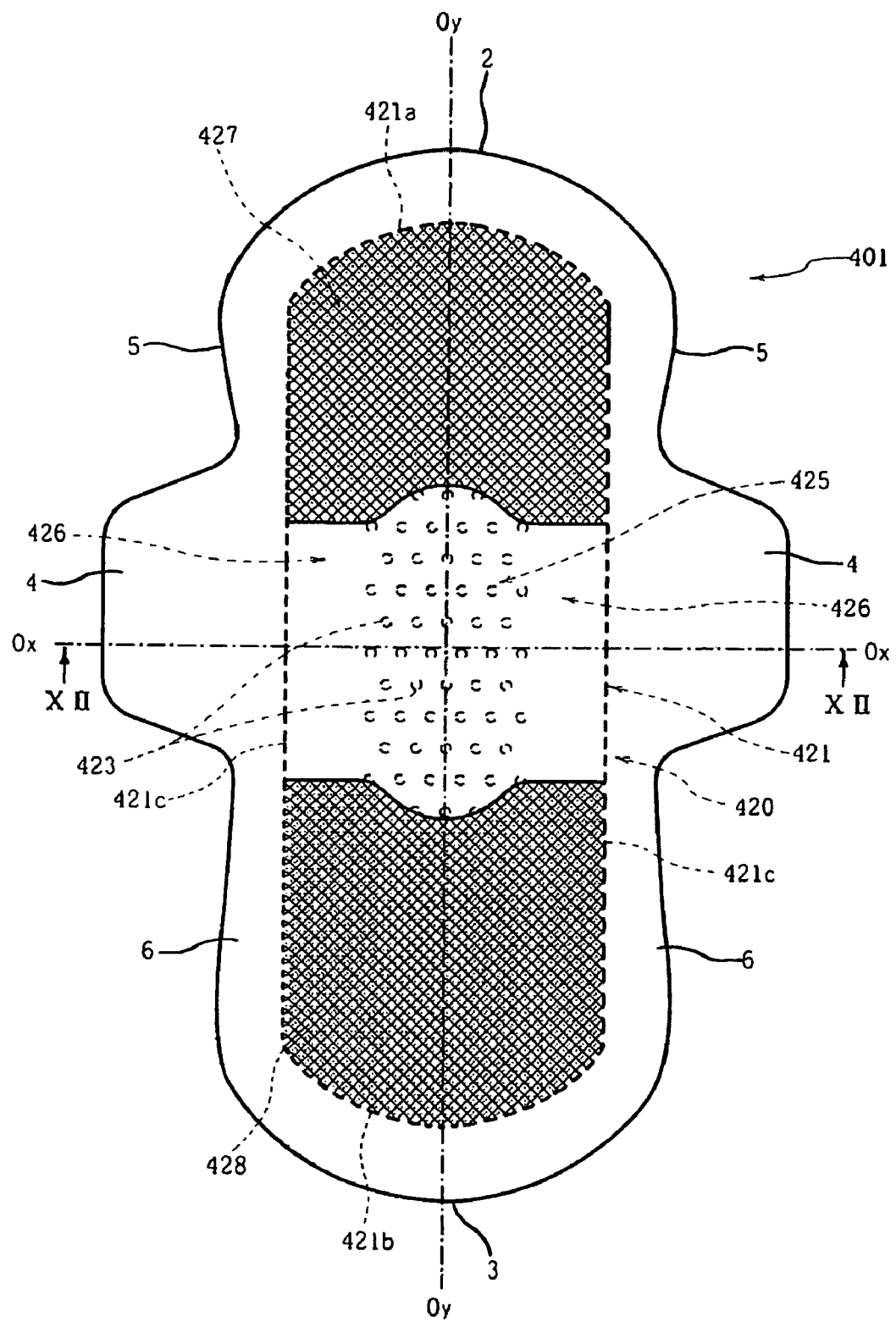
FIG. 10 is a plan view showing a body surface of a sanitary napkin and a liquid-absorbent layer in the context of the sanitary napkin according to a fifth embodiment of the present invention.
Figure 11:
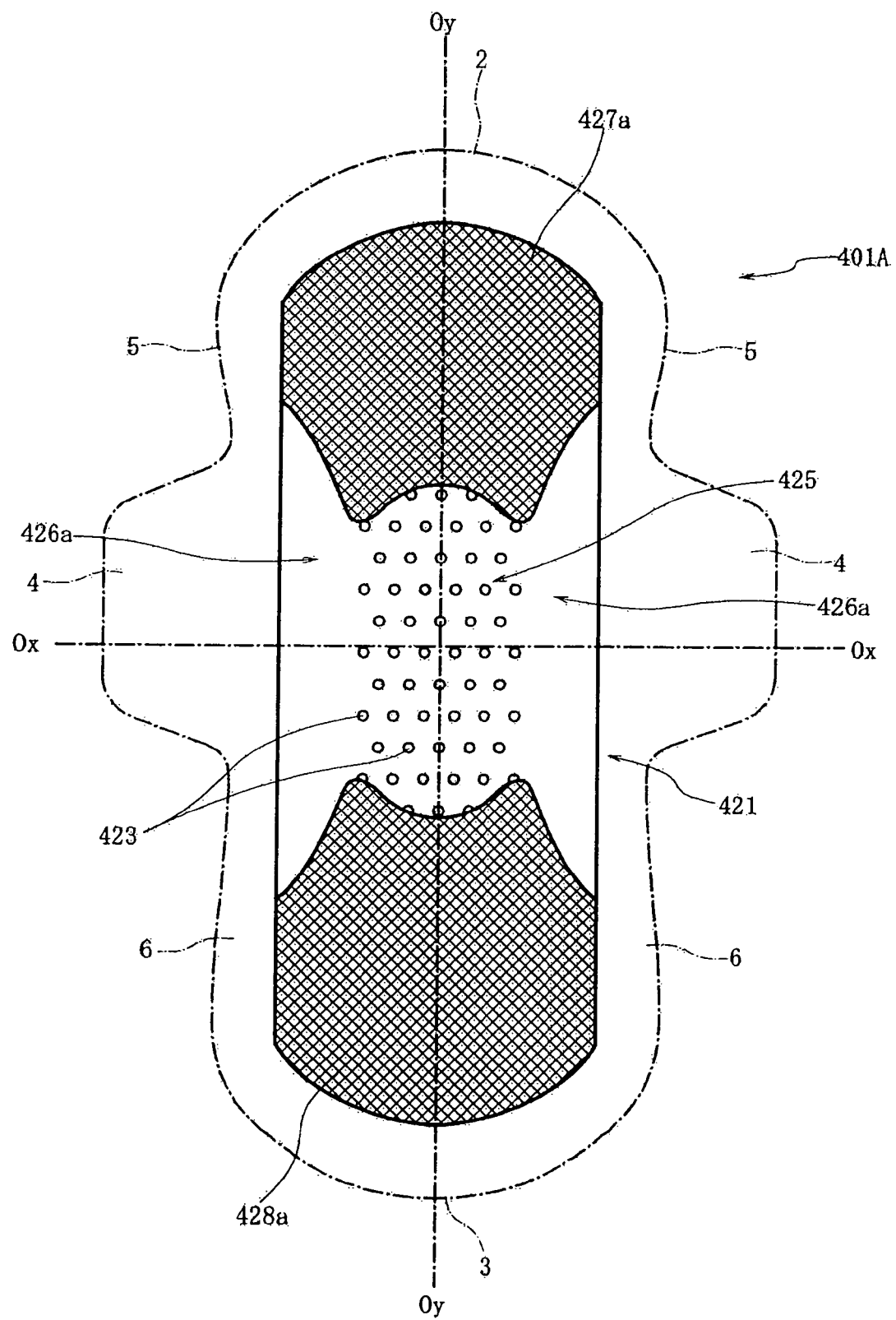
FIG. 11 is a plan view corresponding to FIG. 10, showing a modification of the fifth embodiment.
Figure 12:
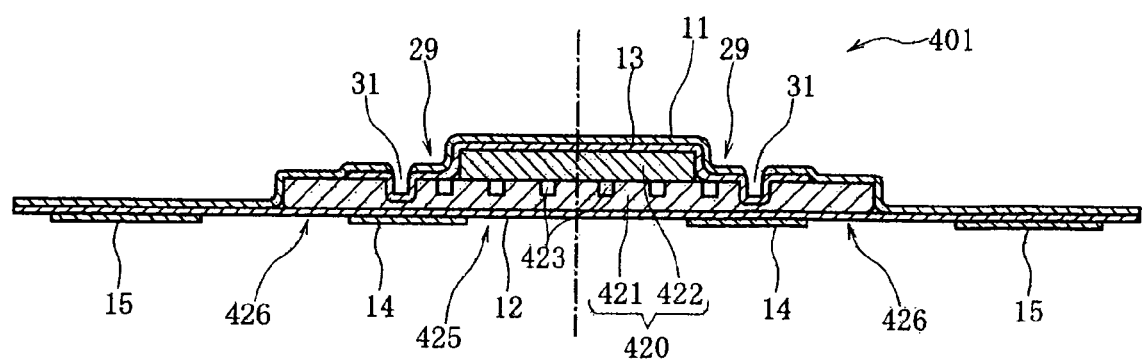
FIG. 12 is a sectional view taken along line XII-XII of FIG. 10.

FIG. 10 is a plan view corresponding to FIG. 1 and showing a body surface of a sanitary napkin and a liquid-absorbent layer contained in the sanitary napkin 401 according to a fifth embodiment of the present invention. FIG. 11 is a plan view corresponding to FIG. 2 and showing a liquid-absorbent layer contained in a sanitary napkin 401A which is a modification of the fifth embodiment. FIG. 12 is a sectional view of the sanitary napkin 401 taken along line XII-XII of FIG. 10.

In FIGS. 10 and 11, the compression line 30 and an upper absorbent core 422 are omitted for clarity. The compression line 30 is formed in the same shape as shown in FIG. 1.

As shown in FIG. 12, a liquid-absorbent layer 420 is constructed of a lower absorbent core 421 and the upper absorbent core 422. As shown in FIG. 10, the lower absorbent core 421 with a front edge 421a, a rear edge 421b, and side edges 421c, 421c has the same plan view contour and size as the lower absorbent core 21 shown in FIGS. 1 to 3. The upper absorbent core 422 has the same size as the upper absorbent core 22 shown in FIGS. 1 to 3 and has the same positional relationship with the outer compression line 31 as the upper absorbent core 22. However, both side portions of the upper absorbent core 422 may overlap with the outer compression line 31 to have both the upper and lower absorbent cores 422, 421 compressed at the outer compression line 31, as in the sanitary napkin 201 shown in FIG. 7.

The lower absorbent core 421 of the sanitary napkin 401 is formed by wrapping fluff pulp in a tissue. In contrast to the foregoing embodiments, the pulp employed as hydrophilic fibers are not bonded together through a binder in the lower absorbent core 421. If desired, superabsorbent polymer (SAP) may be mixed with the fluff pulp.

As shown in FIG. 10, the lower absorbent core 421 is centrally formed with a number of high-density portions 423. The high-density portions 423 may be formed such that the lower absorbent core 421 is pressed (and optionally heated) by pin embossing to locally increase the density of pulp. The high-density portions 423 may be distributed almost over the area where the upper absorbent core 422 is laid on the lower absorbent core 421. The area over which the high-density portions 423 are distributed is vagina-facing region 425, while the areas on both sides of the vagina-facing region 425 are side regions 426 free of the high-density portions 423.

The pulp of the lower absorbent core 421 has a greater basis weight in the vagina-facing region 425 than in the side regions 426. For example, the lower absorbent core 421 may have a basis weight of about 200 to 800 g/m$^2$ in the vagina-facing region 425 and a basis weight of about 50 to 250 g/m$^2$ in the side regions 426. In the vagina-facing region 425 where the pulp has a greater basis weight, the lower absorbent core 421 is entirely compressed to have almost the same thickness as in the side regions 426 and then processed to have the high-density portions 423. Accordingly, the lower absorbent core 421 has a greater stiffness in the vagina-facing region 425 than in the side regions 426.

In the vagina-facing region 425, the lower absorbent core 421 preferably has a Gurley stiffness of at least 3.92 mN (400 mgf). A difference in Gurley stiffness between the vagina-facing region 425 and the side regions 426 is preferably at least 1.96 mN (200 mgf), more preferably at least 2.94 mN (300 mgf). Although not particularly limited, the lower limit of the Gurley stiffness of the side regions 426 is preferably about 0.392 mN (40 mgf).

Due to the stiffness difference, the lower absorbent core 421 provides the hinge lines 29 along the boundaries between the vagina-facing region 425 and the side regions 426. The side regions 426 can easily fold on the hinge lines 29. In the embodiment shown in FIG. 12, however, since the outer compression line 31 lies immediately outside the vagina-facing region 425 over which the high-density portions 423 are distributed, the hinge lines 29 of the lower absorbent core 421 match the outer compression line 31.

As shown in FIG. 10, the lower absorbent core 421 has a front region 427 in front of the vagina-facing region 425 and the side regions 426 and a rear region 428 behind the vagina-facing region 425 and the side regions 426. The basis weight of the lower absorbent core 421 does not differ between the front region 427, the rear region 428, and the side regions 426. The lower absorbent core 421 is locally compressed in the front region 427 and the rear region 428 to have a greater stiffness than in the side regions 426. In the embodiment shown in FIG. 10, the lower absorbent core 421 is embossed in a reticular pattern.

The upper absorbent core 422 is formed by wrapping fluff pulp (and optionally SAP) in a tissue, like the lower absorbent core 421. If desired, the upper and lower absorbent cores 422, 421 may be bonded to each other through an adhesive.

Alternatively, the fluff pulp wrapped in a tissue may have a uniform basis weight. In this case, another absorbent sheet comprising fluff pulp, SAP, and binder such as ethylene-vinyl acetate copolymer (e.g., air-laid pulp) may be laid on the fluff pulp only in the vagina-facing region 425 and then processed by pin embossing to have the high-density portions 423. Conversely, the absorbent sheet (e.g., air-laid pulp) having a uniform basis weight may have the same contour as the lower absorbent core 421. In this case, a fluff pulp layer may be laid on the absorbent sheet only in the vagina-facing region 425 and then processed to have the high-density portions 423. It is also possible to further provide another absorbent sheet (e.g., air-laid pulp) on the fluff pulp layer before formation of the high-density portions 423.

It is also possible to provide the upper absorbent core 422 with the absorbent sheet (e.g., air-laid pulp) as a lower layer and secure the upper absorbent core 422 on the lower absorbent core 421 through an adhesive, thereby further increasing the stiffness of the vagina-facing region 425.

In the sanitary napkin 401, the side regions 426 can easily fold on the hinge lines 29 at both the positions (i) and (ii) shown in FIG. 13. In addition, the vagina-facing region 425, which is resistant to deformation, can easily fit against the vaginal opening. Furthermore, since the stiffness of the lower absorbent core 421 is increased in the front and rear regions 427, 428, the front and rear regions 427, 428 can fit against the crotch without twist or folding.

The sanitary napkin 401A shown in FIG. 11 has the same construction as the sanitary napkin 401 shown in FIG. 10, except that boundaries between side regions 426a and a front region 427a are curved to have their outer ends closer to the front edge 2 of the sanitary napkin 401A and that boundaries between side regions 426a and a rear region 428a are curved to have their outer ends closer to the rear edge 3 of the sanitary napkin 401A.

In the sanitary napkin 401A, the side regions 426a can easily conform to the contour of the thighs 42.

Also in the sanitary napkins 401 and 401A shown in FIGS. 10 to 12, the cuts or the low-density portions may be made in the lower absorbent core 421 along the hinge lines 29 to facilitate folding of the side regions.

In the foregoing embodiments and their modifications, furthermore, three-dimensional gathers may be provided on the body surface of the sanitary napkin to extend in parallel to and on both sides of the longitudinal centerline Oy. The three-dimensional gathers may be constructed of a sheet such as nonwoven fabric and an elastic member for exerting an elastic contractive force between front and rear ends of the three-dimensional gathers. When the sanitary napkin is curved, the three-dimensional gathers rise from the body surface of the sanitary napkin.

The relatively stiff vagina-facing region is effectively prevented from decreasing in width at the position (ii) shown in FIG. 13. Therefore, the three-dimensional gathers can be maintained outside the vagina-facing region so as not to fall on the body surface of the vagina-facing region. Thus, the vagina-facing region can be fully exploited for receiving liquid, while the three-dimensional gathers effectively prevent lateral leakage of menstrual blood.

EXAMPLE (1) Examples and Comparative Examples

For Examples and Comparative Examples, liquid-absorbent layers having the same contour as that show in FIGS. 1 and 2 were prepared. The liquid-absorbent layer was constructed of a lower absorbent core having a length of 210 mm and a width of 75 mm and an upper absorbent core having a length of 80 mm and a width of 35 mm. Both the lower and upper absorbent cores were absorbent sheets (air-laid pulp) comprising 60% by weight of fluff pulp, 26% by weight of SAP, and 14% by weight of emulsion (binder) of ethylene-vinyl acetate copolymer. The upper absorbent core was laid on a longitudinal centerline of the lower absorbent core and secured thereto through a hot-melt type adhesive.

In Examples 5 and 7, the cuts 23 shown in FIG. 2 were arranged to extend the entire length of the upper absorbent core near the side edges of the upper absorbent core. The cuts were made to penetrate through the thickness of the lower absorbent core and arranged in the form of a dashed line parallel to the longitudinal centerline. Such cuts were not provided in the other Examples and Comparative Examples.

The individual liquid-absorbent layers were interposed between a topsheet and a backsheet. The topsheet was a through-air bonded nonwoven fabric having a basis weight of 40 g/m$^2$; the backsheet was a polyethylene film having a basis weight of 20 g/m$^2$. The topsheet and the backsheet were bonded to each other through a hot-melt type adhesive outside the liquid-absorbent layer.

In Examples and Comparative Examples, the basis weights of the upper and lower absorbent cores were as follows:

Example 1

For the lower absorbent core, two absorbent sheets each having a basis weight of 160 g/m$^2$ were bonded to each other to have a total basis weight of 320 g/m$^2$. For the upper absorbent core, a single absorbent sheet having a basis weight of 160 g/m$^2$ was used.

Example 2

For the lower absorbent core, two absorbent sheets having a basis weight of 160 g/m$^2$ and a basis weight of 60 g/m$^2$ were bonded to each other to have a total basis weight of 220 g/m$^2$. For the upper absorbent core, a single absorbent sheet having a basis weight of 160 g/m$^2$ was used.

Example 3

For the lower absorbent core, a single absorbent sheet having a basis weight of 160 g/m$^2$ was used. For the upper absorbent core, a single absorbent sheet having a basis weight of 160 g/m$^2$ was used.

Example 4

For the lower absorbent core, a single absorbent sheet having a basis weight of 100 g/m$^2$ was used. For the upper absorbent core, a single absorbent sheet having a basis weight of 160 g/m$^2$ was used.

Example 5

For the lower absorbent core, a single absorbent sheet having a basis weight of 160 g/m$^2$ was used. For the upper absorbent core, a single absorbent sheet having a basis weight of 100 g/m$^2$ was used. The cuts were made along the hinge lines.

Example 6

For the lower absorbent core, a single absorbent sheet having a basis weight of 160 g/m$^2$ was used. For the upper absorbent core, a single absorbent sheet having a basis weight of 100 g/m$^2$ was used.

Example 7

For the lower absorbent core, a single absorbent sheet having a basis weight of 160 g/m$^2$ was used. For the upper absorbent core, a single absorbent sheet having a basis weight of 160 g/m$^2$ was used. The cuts were made along the hinge lines.

Comparative Example 1

For the lower absorbent core, two absorbent sheets having a basis weight of 160 g/m² and a basis weight of 100 g/m² were bonded to each other to have a total basis weight of 260 g/m². The upper absorbent core was not provided.

Comparative Example 2

For the lower absorbent core, two absorbent sheets having a basis weight of 160 g/m² and a basis weight of 60 g/m² were bonded to each other to have a total basis weight of 220 g/m². For the upper absorbent core, a single absorbent sheet having a basis weight of 60 g/m² was used.

Comparative Example 3

For the lower absorbent core, a single absorbent sheet having a basis weight of 60 g/m² was used. For the upper absorbent core, a single absorbent sheet having a basis weight of 160 g/m² was used.

(2) Measurement of Stiffness

Stiffness was measured using a Gurley Type Stiffness Tester (No. 311) manufactured by YASUDA SEIKI SEISAKUSHO LTD. For measurement of stiffness of the vagina-facing region, a rectangular test sample where the upper and lower absorbent cores were bonded to each other through an adhesive, was cut out of the liquid-absorbent layer to have a size of 38 mm×25 mm with its length aligned with the lateral direction of the sanitary napkin. Stiffness was measured longitudinally of the test sample. For measurement of stiffness of the side region, another rectangular test sample was cut out of the lower absorbent core to have a size of 38 mm×25 mm with its length aligned with the lateral direction of the sanitary napkin. Stiffness was measured longitudinally of the test sample.

Stiffness was measured in "mgf", but converted into "mN" in Table 1. Table 1 shows Gurley stiffness of the vagina-facing region, Gurley stiffness of the side region, and stiffness difference for respective Examples and Comparative Examples.

(3) Wear-Test

Wear-test was performed using a silicon dummy manufactured by KATO TECH CO., LTD. The dummy was a replica of a woman's lower body and set to have a minimum distance of 35 mm between the thighs. An undergarment was put on the dummy with the sanitary napkin adhered on an inner side of a crotch part of the undergarment.

When the side regions of the liquid-absorbent layer could fold downward along the hinge lines on the way to the crotch and the vagina-facing region could be brought into contact with the vaginal opening in an almost flat, undeformed state, the sanitary napkin was deemed as acceptable. The wear-test was performed 10 times for each sanitary napkin.

Table 1 shows wear-test results, where "○" represents that the sanitary napkin was accepted 10 times, "Δ" represents that the sanitary napkin was accepted 6 to 9 times, and "X" represent that the sanitary napkin was accepted 5 times or less.

TABLE 1

| | Stiffness (mN) of Vagina-facing region | Stiffness (mN) of Side region | Stiffness Difference | Wear-Test Result |
| --- | --- | --- | --- | --- |
| Ex. 1 | 19.8 | 9.44 | 10.4 | ○ |
| Ex. 2 | 11 | 3.68 | 7.32 | ○ |
| Ex. 3 | 9.44 | 2.38 | 7.06 | ○ |
| Ex. 4 | 5.01 | 0.49 | 4.52 | ○ |
| Ex. 5 | 5.01 | 1.1 | 3.91 | ○ |
| Ex. 6 | 5.01 | 2.38 | 2.63 | ○ |
| Ex. 7 | 9.44 | 1.1 | 8.34 | ○ |
| Com. Ex. 1 | 5.01 | 5.01 | 0 | X |
| Com. Ex. 2 | 5.16 | 3.68 | 1.48 | Δ |
| Com. Ex. 3 | 3.68 | 0.49 | 3.19 | X |

From Table 1, it is understood that the vagina-facing region preferably has a Gurley stiffness of at least 3.92 mN (400 mgf) and the difference in Gurley stiffness between the vagina-facing region and the side regions is preferably at least 1.96 mN (200 mgf). The stiffness difference is more preferably at least 2.94 mN (300 mgf).

Although the present invention has been illustrated and described with respect to exemplary embodiments thereof, it should be understood by those skilled in the art that the foregoing and various other changes, omission and additions may be made therein and thereto, without departing from the spirit and scope of the present invention. Therefore, the present invention should not be understood as limited to the specific embodiments set out above but should be understood to include all possible embodiments which can be embodied within a scope encompassed and equivalent thereof with respect to the feature set out in the appended claims.

What is claimed is:

1. A sanitary napkin comprising
a liquid-permeable topsheet,
a backsheet, and
a liquid-absorbent layer disposed between the topsheet and the backsheet,
wherein the liquid-absorbent layer has a vagina-facing region on a longitudinal centerline of the sanitary napkin configured to face only a wearer's vaginal opening and side regions on both sides of the vagina-facing region configured to face only areas of a wearer's crotch other than the wearer's vaginal opening,
wherein the liquid-absorbent layer comprises a lower absorbent core and an upper absorbent core disposed on a body surface of the lower absorbent core, wherein the upper absorbent core has a smaller area than the lower absorbent core and lies only within the vagina-facing region of the liquid absorbent layer,
wherein said liquid-absorbent layer further comprises two hinge lines, each extending in the longitudinal direction along opposite lateral boundaries between the vagina-facing region and the side regions of the liquid absorbent layer, and
wherein the hinge lines each comprises a plurality of linear cuts extending, along a maximum dimension of the linear cuts, in intervals along a single line in the longitudinal direction of the sanitary napkin and penetrating at least a portion of a thickness of the lower absorbent core, there being no linear cuts in the vagina-facing region,
said sanitary napkin further comprising outer compression lines, wherein the liquid absorbent layer is compressed together with the topsheet, on both sides of the longitudinal centerline and extend longitudinally of the sanitary napkin, wherein the outer compression lines are laterally located entirely outside of the hinge lines.

2. The sanitary napkin of claim 1, wherein the vagina-facing region has a plurality of high-density portions where the lower absorbent core is locally compressed.

3. The sanitary napkin of claim 2, wherein the upper absorbent core is secured on the lower absorbent core by providing laterally opposing side portions of the upper absorbent core with compression portions where the upper and lower absorbent cores are compressed together.

4. The sanitary napkin of claim 2, wherein the lower absorbent core has a greater basis weight and a greater density in the vagina-facing region than in the side regions.

5. The sanitary napkin of claim 2, wherein the liquid-absorbent layer has a front region in front of the vagina-facing region and the side regions and a rear region behind the vagina-facing region and the side regions, and the lower absorbent core has a greater bending stiffness in the front and rear regions than in the side regions.

6. The sanitary napkin of claim 1, wherein compression portions where the liquid-absorbent layer is compressed and recessed together with the topsheet lie on both sides of the longitudinal centerline and extend longitudinally of the sanitary napkin, and the hinge lines are located inside the compression portions.

7. The sanitary napkin of claim 1, wherein compression portions where the liquid-absorbent layer is compressed and recessed together with the topsheet lie on both sides of the longitudinal centerline and extend longitudinally of the sanitary napkin, and the hinge lines are located outside the compression portions.

8. The sanitary napkin of claim 1, wherein a difference in Gurley stiffness between the vagina-facing region and the side regions is at least 1.96 mN.

9. The sanitary napkin of claim 1, wherein the hinge lines lie on both sides of the longitudinal centerline and extend in parallel to the longitudinal centerline.

10. The sanitary napkin of claim 1, wherein the hinge lines lie on both sides of the longitudinal centerline and extend arcuately to have an intermediate portion closer to the longitudinal centerline, the intermediate portion extending along the single line in the longitudinal direction of the sanitary napkin.

11. The sanitary napkin of claim 1, wherein the absorbent core is an absorbent sheet whose hydrophilic fibers are bonded together through a binder.

12. The sanitary napkin of claim 11, wherein the absorbent sheet is further heated and pressed.

13. The sanitary napkin of claim 1, wherein the cuts penetrate into low-density portions of the lower absorbent core where a density of the lower absorbent core is locally decreased.

14. The sanitary napkin of claim 1, wherein a cushion layer having a lower density than the absorbent core is disposed between the liquid-absorbent layer and the topsheet.

15. The sanitary napkin of claim 1, wherein each of the pair of hinge lines is co-extensive in the longitudinal direction with the upper absorbent core.

* * * * *